(12) United States Patent
Landis et al.

(10) Patent No.: US 6,745,396 B1
(45) Date of Patent: Jun. 8, 2004

(54) ARTICULATING SUPPORT ARM APPARATUS FOR HEAD-WORN DEVICES (75) Inventors: Timothy J. Landis, Loomis, CA (US); Kyle D. Fields, El Dorado Hills, CA (US); Clay D. Allen, Elk Grove, CA (US)

(73) Assignee: OP-D-OP, Inc., Roseville, CA (US)

( * ) Notice: Subject to any disclaimer, the term of this patent is extended or adjusted under 35 U.S.C. 154(b) by 0 days.

(21) Appl. No.: 10/263,247

(22) Filed: Oct. 1, 2002

Related U.S. Application Data (63) Continuation of application No. 09/888,081, filed on Jun. 21, 2001, now Pat. No. 6,490,757, which is a continuation of application No. 09/115,417, filed on Jul. 14, 1998, now Pat. No. 6,278,788, which is a continuation-in-part of application No. 08/962,864, filed on Nov. 3, 1998, now Pat. No. 5,933,862, which is a continuation of application No. 08/671,700, filed on Jun. 28, 1996, now Pat. No. 5,682,608.

(51) Int. Cl.[7] .............................. A61F 9/00; E05D 11/10
(52) U.S. Cl. ................... 2/12; 16/228; 16/324
(58) Field of Search .......................... 2/1, 15, 12, 171, 2/209.13, 454; 16/228, 297, 232, 342, 328, 324, 319, 386; 403/97, 151, 161; 351/153, 115, 111, 118, 119, 121, 123, 140, 41

(56) References Cited

U.S. PATENT DOCUMENTS

| | | | |
|---|---|---|---|
| 1,440,713 A | 1/1923 | Ausbourne | |
| 2,094,236 A | 9/1937 | Hempel | |
| 2,412,120 A | 12/1946 | Bouchard | |
| 3,110,057 A | 11/1963 | Urich | |
| 3,317,225 A | 5/1967 | Cooper | |
| 3,383,707 A | 5/1968 | McNeill | |
| 3,671,111 A | 6/1972 | Okner | |
| 3,744,085 A | 7/1973 | Griego | |
| 3,874,775 A | 4/1975 | Lazarus | |
| 4,186,905 A | 2/1980 | Brudy | |
| 4,731,896 A | 3/1988 | de La Tour | |
| 4,787,727 A | 11/1988 | Boodman et al. | |
| 4,974,289 A | 12/1990 | Piard | |
| 5,131,094 A | 7/1992 | Ackerman | |
| 5,289,592 A | 3/1994 | Paivarinta | |
| 5,503,497 A | 4/1996 | Dudley et al. | |
| 5,589,895 A | 12/1996 | Mizuno | |
| 5,592,243 A | 1/1997 | Chao | |
| 5,623,322 A | 4/1997 | Hirschman et al. | |
| 5,628,092 A | 5/1997 | Harris et al. | |
| 5,631,718 A | 5/1997 | Markovitz et al. | |
| 5,682,608 A | 11/1997 | Landis | |
| 5,692,522 A | * 12/1997 | Landis | 2/15 |
| 5,933,862 A | 8/1999 | Landis | |
| 5,975,693 A | 11/1999 | Malfroy et al. | |
| 6,278,788 B1 | 8/2001 | Landis | |

FOREIGN PATENT DOCUMENTS

| | | |
|---|---|---|
| EP | 0 534 592 A1 | 3/1993 |
| FR | 2735879 | 12/1996 |
| WO | WO 99/02059 | 1/1999 |

\* cited by examiner

*Primary Examiner*—Rodney M. Lindsey
(74) *Attorney, Agent, or Firm*—John P. O'Banion (57) ABSTRACT

A head worn apparatus having a pair of rearwardly disposed elongated support arm assemblies having movable portions which are positionally adjustable to provide increased wearer comfort attached to a head-worn device such as a visor or eyeglasses. The support arm assemblies each include a an articulating segment and/or head gripping region pivotally coupled to the head-worn apparatus. The articulating segment include means for providing a constant inward compressive force by means of increased resistance for rotating articulating segments outwardly, thereby securing the head-worn device onto a wearer's head.

3 Claims, 7 Drawing Sheets

ARTICULATING SUPPORT ARM APPARATUS FOR HEAD-WORN DEVICES

CROSS-REFERENCE TO RELATED APPLICATIONS

This application is a continuation of application Ser. No. 09/888,081 filed on Jun. 21, 2001, now U.S. Pat. No. 6,490,757, which is a continuation of application Ser. No. 09/115,417 filed on Jul. 14, 1998, now U.S. Pat. No. 6,278,788, which is a continuation-in-part of U.S. application Ser. No. 08/962,864 filed on Nov. 3, 1997, now U.S. Pat. No. 5,933,862, which is a continuation of U.S. application Ser. No. 08/671,700 filed on Jun. 28, 1996, now U.S. Pat. No. 5,682,608, which is incorporated herein by reference.

STATEMENT REGARDING FEDERALLY SPONSORED RESEARCH OR DEVELOPMENT

Not Applicable

REFERENCE TO A COMPUTER PROGRAM APPENDIX

Not Applicable

BACKGROUND OF THE INVENTION

1. Field of the Invention

The present invention pertains generally to head worn visors and like devices, and more particularly to pivotally adjustable support arms and support pads for head-worn devices.

2. Description of the Background Art

Head worn visors are frequently utilized by golfers, tennis players, joggers, and other persons engaged in outdoor activities to reduce glare to the eyes and to prevent sunburn. Head worn visors are also commonly used in dental, medical and other professions to support face shields, eye shields, lights, reflectors, mirrors, magnifying optics, tinted glass or other apparatus from a wearer's head.

Conventional head worn visors typically comprise a headband with a forwardly disposed bill or shade and a pair of rearwardly disposed resilient arms which partially encircle and tensionally engage the sides of a wearer's head in order to hold or support the visor on the wearer's head. In another typical arrangement, the rearwardly disposed arms generally encircle the wearer's head and are coupled or joined together in the back of the wearer's head.

The aforementioned conventional visor types share a common deficiency; they are uncomfortable to wear, particularly for extended periods of time. In order to minimize discomfort, the visor must be frequently repositioned. This problem is most readily apparent with head worn visor devices having resilient, rearwardly disposed arms which tensionally engage the wearer's head, since the amount of force or tension applied by the resilient arms to the wearer's head generally cannot be controlled or adjusted, and the force or tension is applied to a relatively small area of the wearer's head. This is a particular problem for physicians, dentists, welders, and other persons who rely on face shields or other devices supported by a head worn visor since these persons frequently have both hands occupied in difficult or complex procedures and cannot free their hands to positionally adjust the head visor to a new position to increase comfort. Furthermore, these persons often wear eyeglasses with corrective lenses during the performance of these procedures, and, as is common to most eyeglasses, the arms of the eyeglass frame hook around the rear of the wearer's ear. Using the ears to additionally support a visor apparatus would significantly contribute to the discomfort of the wearer.

It will further be appreciated that eyeglasses suffer from the same aforementioned deficiencies; that is, they can be uncomfortable to wear because of an inadequate side support mechanism.

Accordingly, there is a need for an articulating support arm apparatus for head-worn devices such as visors and glasses which provides for positional control of rearwardly disposed tails instead of, which allows adjustment of the amount of tension or force exerted by the tails against the sides of the wearer's head, and which maintains the adjusted tension or force exerted by the tails against the sides of the wearer's head. The present invention satisfies these needs, as well as others, and generally overcomes the deficiencies present in the background art.

SUMMARY OF THE INVENTION

The present invention pertains to an articulating support arm apparatus which provides increased wearer comfort. In general terms, the invention comprises a pair of support arm assemblies that can be coupled to the headband of a visor or to the frame of eyeglasses. Each support arm assembly includes a head gripping pad, an articulating member for positionally adjusting the head gripping pad relative to the support arm and an articulating adjustment means for positionally adjusting the articulating member and the head gripping pad. Articulating adjustment means includes means to create a greater holding force on the articulating member so as to provide the head gripping pad a more constant and secure grip around a wearer's head.

The articulating adjustment means preferably comprises sleeves on the articulating members which pivotally couple to a sleeve on the rear portion of a headband and posts on the articulating members which pivotally engage the sockets on the head gripping pads. Alternatively, the apparatus can be connected to an eyeglass frame or to short support arms connected to an eyeglass frame. A plunger having a plurality of teeth or serrations is inserted within the sleeves, with the serrations on the plunger structured and configured to reversibly intermesh with the serrations within the sleeve of the headband to provide pivotal articulation in a ratcheting fashion.

The invention is utilized by placing it on the wearer's head with the wearer's head generally positioned between the first and second support arm assemblies. The articulating members and/or articulating head gripping pads are pivotally adjusted to desired positions to accommodate the wearer's head by pushing on or otherwise applying force to the articulating members and/or head gripping pads. The amount of tension applied to the wearer's head by the first and second support arm assemblies is controlled by pivotally adjusting the position of the articulating members. Optionally, the articulating members and head gripping pads are detachable and interchangeable so that the wearer can adjust or control the amount of head contact surface area by selecting particular articulating members and head gripping pads.

An object of the invention is to provide an articulating support apparatus which may be pivotally adjusted to fit the head of individual wearers.

Another object of the invention is to provide an articulating support apparatus which is comfortable to wear for extended periods of time.

Another object of the invention is to provide a support apparatus with articulating arm members such that greater frictional resistance is encountered when rotating the arm members in a direction away from the wearer's head.

Still another object of the invention is to provide articulating arm members which are adaptable to head-worn devices such as visors and eyeglasses.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Referring more specifically to the drawings, for illustrative purposes the present invention is embodied in the apparatus generally shown in FIG. 1 through FIG. 7. It will be appreciated that the apparatus may vary as to configuration and as to details of the parts without departing from the basic concepts as disclosed herein.

Figure 1:
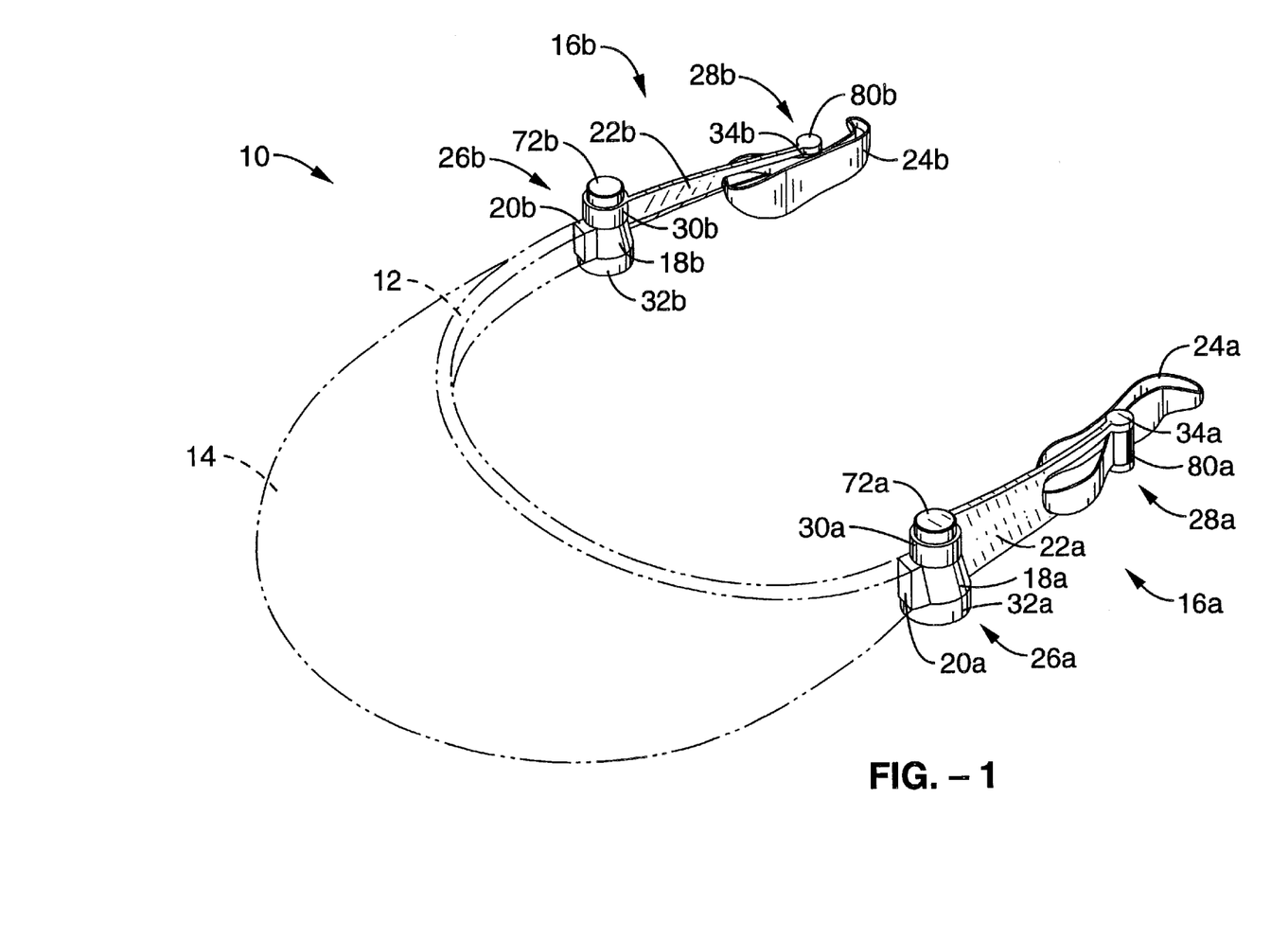
FIG. 1 is a perspective view of articulating support arms in accordance with the present invention coupled to a visor and headband, which are shown in phantom.

Referring first to FIG. 1, an articulating visor apparatus 10 employing articulating support arms in accordance with the invention is generally shown. Visor apparatus 10 generally includes a headband 12 and a forwardly disposed bill or shade 14 joined to head band 12. The invention comprises a pair of support arm assemblies 16a, 16b having a pair of center sleeves 18a, 18b that can be coupled to the rear end 20a, 20b of head band 12 or the like. Headband 12, shade 14 and center sleeves 18a, 18b may be integrally formed from a single piece of resilient material such as polyethylene sheet, or may comprise separate portions which are joined together by adhesives, melt bonding, or like means. Support arm assemblies 16a, 16b include articulating members 22a, 22b that are pivotally coupled to center sleeves 18a, 18b, respectively, and head gripping pads 24a, 24b that are pivotally coupled to articulating members 22a, 22b, respectively.

The length, structure and configuration of articulating members 22a, 22b may be varied as required for different wearer head sizes or for particular applications of the invention. Preferably, articulating members 22a, 22b are of a generally elongate shape as shown. Articulating member 22a has a first or front end 26a and a second or back end 28a, and articulating member 22b likewise includes a first or front end 26b and a second or back end 28b. An upper sleeve 30a and a lower sleeve 32a are joined to first end 26a of articulating member 22a, and a generally cylindrical post 34a is joined to second end 28a of articulating member 22a. Similarly, an upper sleeve 30b and a lower sleeve 32b are attached to first end 26b of articulating member 22b, and a generally cylindrical post 34b is attached to second end 28b of articulating member 22b.

Figure 2:
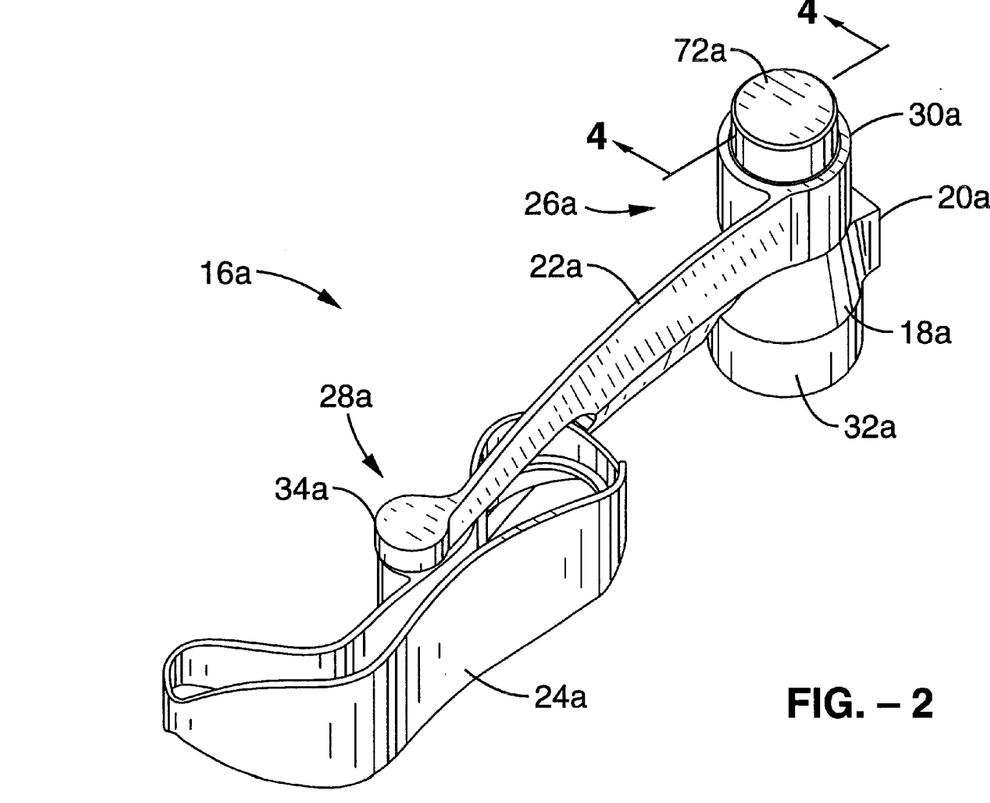
FIG. 2 is a detailed perspective view of a left support arm assembly shown in FIG. 1.
Figure 3:
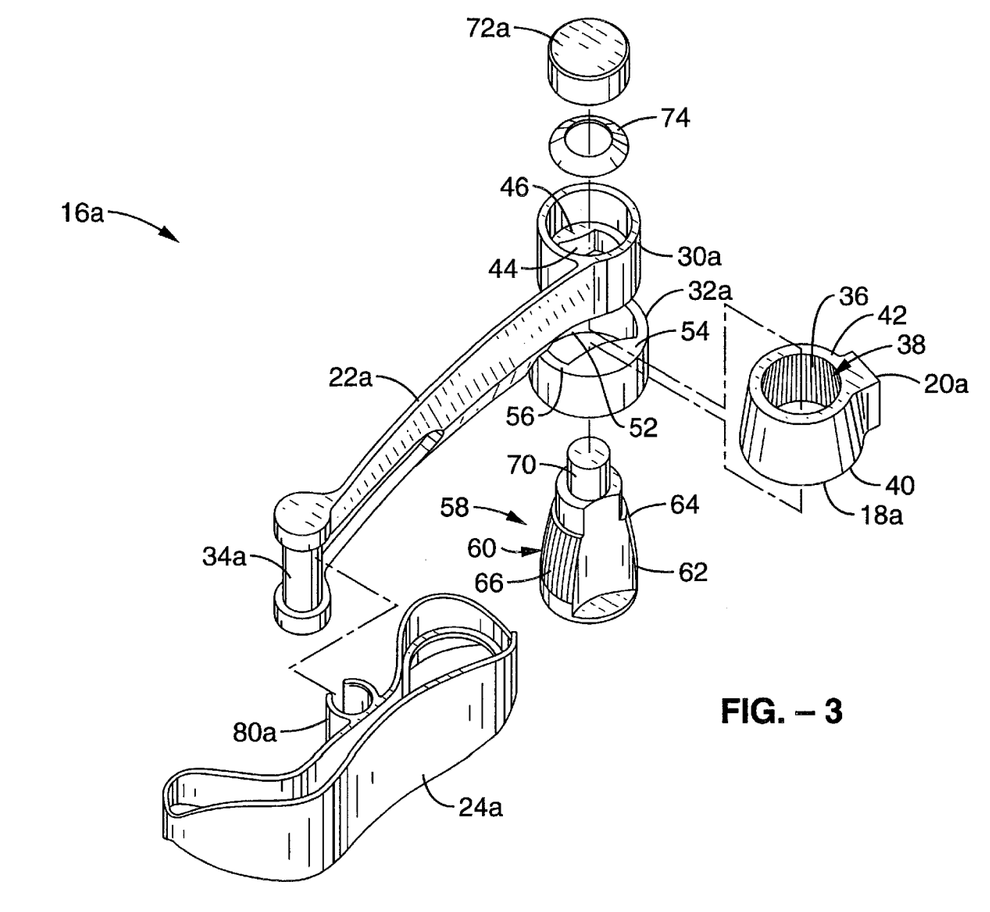
FIG. 3 is a detailed exploded view of the left support arm assembly shown in FIG. 2.
Figure 4:
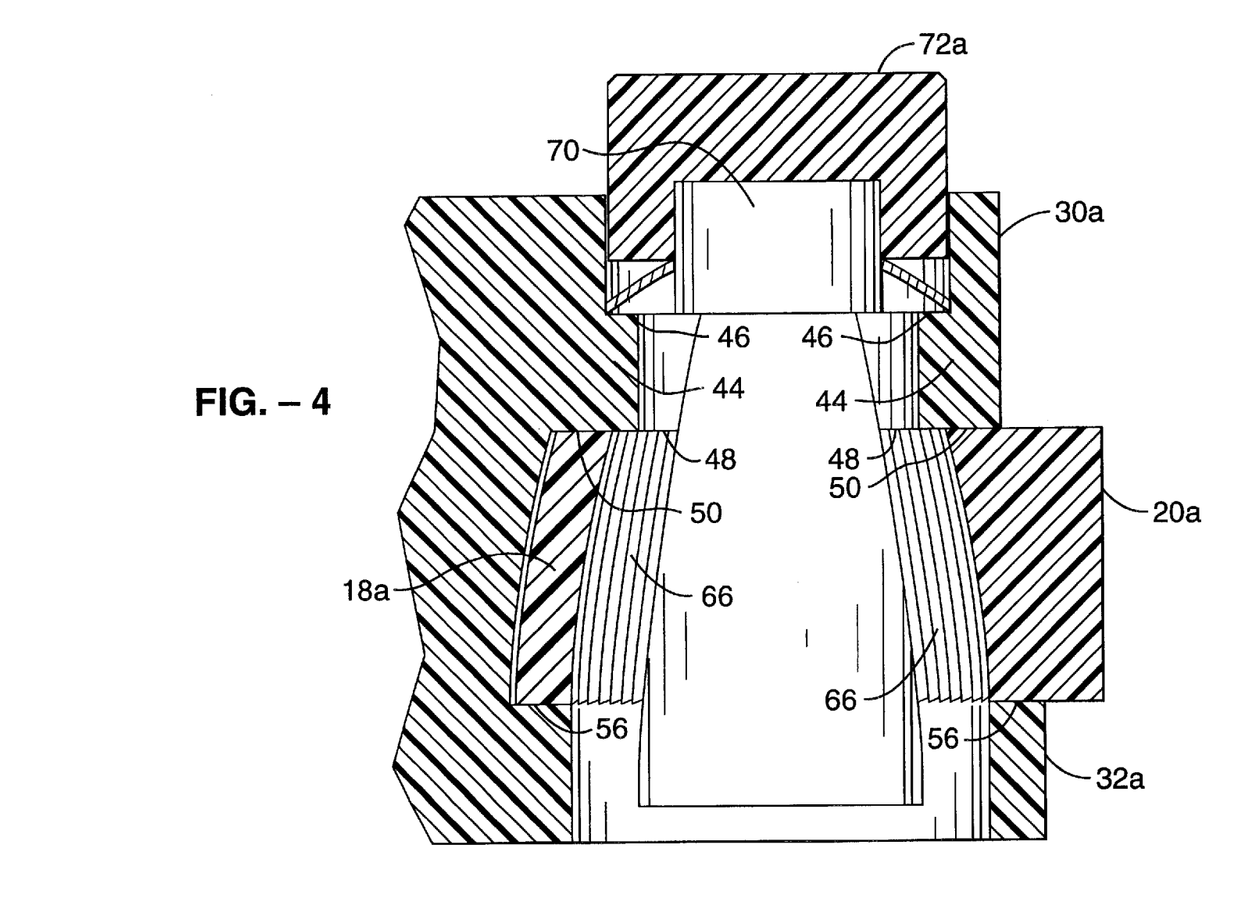
FIG. 4 is a cross-sectional view of the articulating adjustment means portion of the apparatus taken along line 4—4 of FIG. 2.

Referring also to FIG. 2, FIG. 3 and FIG. 4, the details of support arm assembly 16a are depicted. Although not depicted in detail, support arm assembly 16b comprises similar mirror-image components shown and described for support arm assembly 16a. Accordingly, support arm assembly 16b is configured and functions in the same manner as support arm assembly 16a.

It can be seen that center sleeve 18a includes a plurality of longitudinally oriented serrations 36 disposed circumferentially around the inner surface 38 of center sleeve 18a. The inner diameter of center sleeve 18a tapers from the bottom 40 to the top 42 of center sleeve 18a in a conical fashion. A first pair of arc-shaped ledges 44, preferably spaced 180° apart, protrude inwardly within upper sleeve 30a, forming steps 46 within upper sleeve 30a. The bottom surface 48 of ledges 44 are flush with the bottom surface 50 of upper sleeve 30a. Similarly, a second pair of arc-shaped ledges 52, preferably spaced 180° apart, protrude inwardly within lower sleeve 32a. The upper surface 54 of ledges 52 are flush with the upper surface 56 of lower sleeve 32a. The general effect of first pair of arc-shaped ledges 44 and second pair of arc-shaped ledges 52 is to form non-circular shaped apertures within upper sleeve 30a and lower sleeve 32a, respectively.

Figure 5:
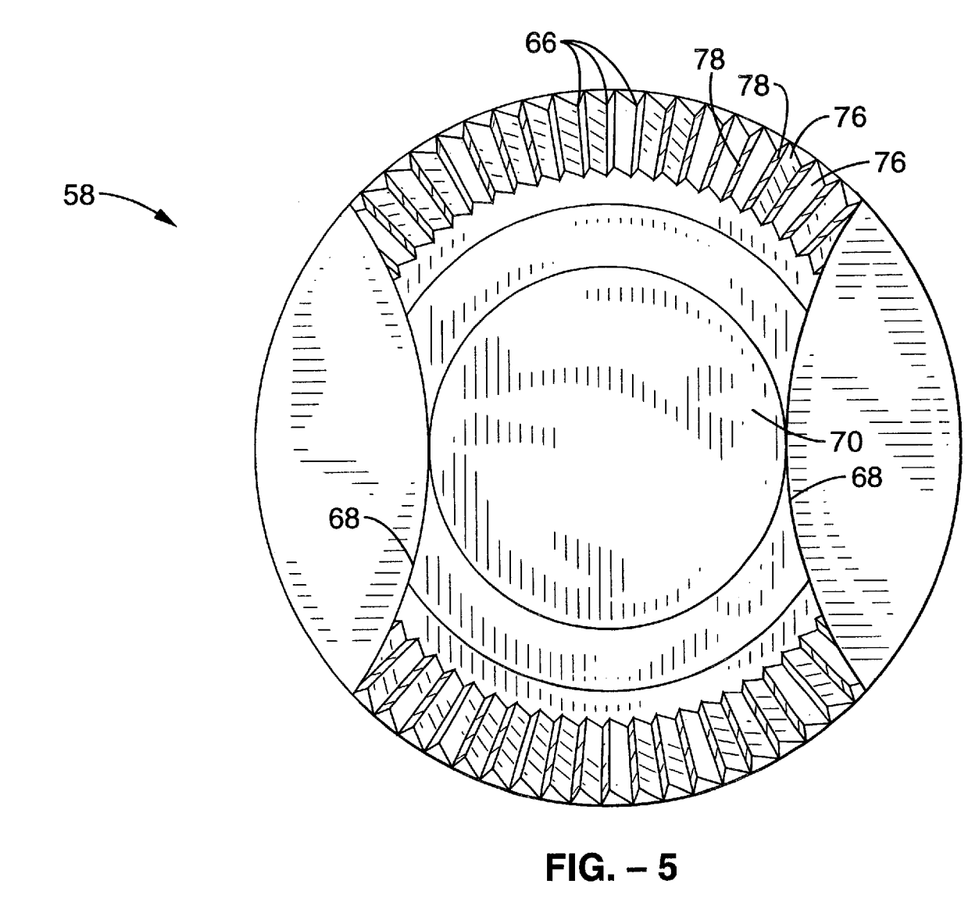
FIG. 5 is a top plan view of the plunger shown in FIG. 3.

Referring additionally to FIG. 5, center sleeve 18a is disposed between upper sleeve 30a and lower sleeve 32a with center sleeve 18a coupled to articulating member 22a by a plunger 58 inserted upward through lower sleeve 32a, center sleeve 18a and upper sleeve 30a. Plunger 58 includes a conical section 60 tapering from bottom 62 to top 64 of conical section 60 with a degree of taper matching that within center sleeve 18a. Longitudinally oriented serrations 66 are disposed circumferentially around conical section 60. Plunger 58 includes a pair of cut-outs 68, preferably spaced 180° apart, and configured to engage adjacent first arc-shaped ledges 44 and second arc-shaped ledges 52 such that rotation of upper sleeve 30a and lower sleeve 32a causes a corresponding rotation of plunger 58 engaged therein. It is contemplated that any generally non-circular aperture within upper sleeve 30a and lower sleeve 32a will meet the objective of preventing plunger 58 rotation relative to upper sleeve 30a and lower sleeve 32a when plunger 58 is inserted therein.

Plunger 58 also includes an extended tip 70 onto which a tab 72a is press fitted to retain plunger 58 within lower sleeve 32a, center sleeve 18a and upper sleeve 30a. The design allows for limited longitudinal movement of plunger 58 when engaged therein. An annular spring 74 inserted between tab 72a and steps 46 of upper sleeve 30a biases plunger 58 upward. When plunger 58 is biased to its uppermost position, serrations 66 on plunger 58 frictionally engage serrations 36 within center sleeve 18a, thereby rendering articulating member 22a fixed in position. As tab 72a is depressed, serrations 66 on plunger 58 disengage from serrations 36 within center sleeve 18a, thereby allowing for frictional rotation of upper sleeve 30a and lower sleeve 32a, thus allowing for adjustment of articulating member 22a. Serrations 66 on plunger 58 along with serrations 36 in center sleeve 18a are angled such that a lower frictional resistance is encountered when articulating member 22a is rotated counter-clockwise than when rotated clockwise. This is because serrations 66 have clockwise facing lands 76 that are longer, measured tangentially, than counter-clockwise facing lands 78. Serrations 36 within center sleeve 18a are similarly but reversibly configured to allow for proper engagement and meshing thereon.

The converse is applicable to articulating member 22b, wherein a lower frictional resistance is encountered when articulating member 22b is rotated clockwise than when rotated counter-clockwise. Therefore, when apparatus 10 is placed on a wearer's head (not shown), positional adjustment of articulating members 22a, 22b in an inward direction (towards the wearer's head) applies greater compressive force to head gripping pads 24a, 24b, allowing the wearer to more firmly affix the visor 10 on the wearer's head. A looser fit is achieved by positionally adjusting articulating members 22a, 22b outward or away from the wearer's head after depressing tab 72a and/or tab 72b. Thus, through the articulating motion of the articulating members 22a, 22b, the wearer can precisely fit the head visor apparatus 10 to his or her head to provide maximum comfort.

Head gripping pads 24a, 24b include sockets 80a, 80b which pivotally engage cylindrical posts 34a, 34b of articulating members 22a, 22b. Sockets 80a, 80b are preferably made of resilient material so that posts 34a, 34b reversibly snap fit into sockets 80a, 80b, allowing disassembly from articulating members 22a, 22b for cleaning or interchanging with other head gripping pads of different configuration.

Additionally, sockets 80a, 80b on head gripping pads 24a, 24b, respectively, are offset from the longitudinal center of the head gripping pads 24a, 24b. This configuration allows the wearer to make the overall length of support arm assemblies 16a, 16b longer or shorter by removing head gripping pads 24a, 24b, turning them over, and then reinstalling them. While the length change may be small, it can effect a significant change in comfort to the wearer. Note also that the posts 34a, 34b of articulating members 22a, 22b are offset from the longitudinal axis of the members to allow for a greater range of pivotal movement of head gripping pads 24a, 24b before contacting articulating members 22a, 22b. Head gripping pads 24a, 24b are covered with open cell foam, giving them a softer and more comfortable feel when worn.

Note also that head gripping pads 24a, 24b, can be omitted if desired. When omitting head gripping pads 24a, 24b, posts 34a, 34b on back ends 28a, 28b of articulating members 22a, 22b are also preferably omitted. In this arrangement it is also preferably to provide a slightly curved head-accommodating shape or inner surface to articulating members 22a, 22b to increase wearer comfort. Cushioning means and/or sweat absorption means may also be used in association with articulating members 22a, 22b.

Figure 6:
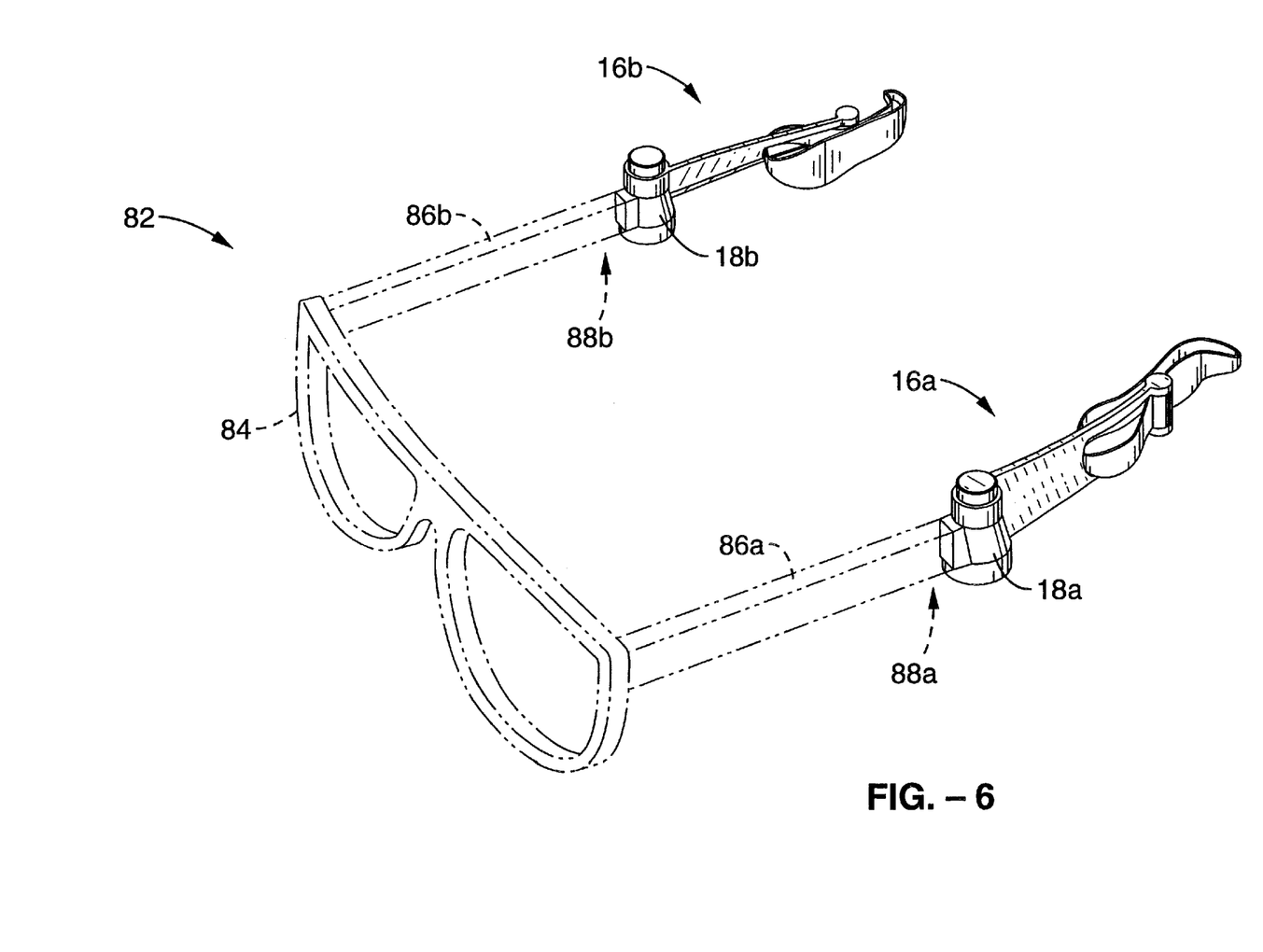
FIG. 6 is a perspective view of the articulating support arms of the present invention coupled to temples of eyeglasses shown in phantom.

Referring to FIG. 6, an alternate embodiment 82 employing the present invention are shown wherein like numerals denote like parts. Eyeglass frames 84 generally comprises temple arms 86a, 86b coupled to support arm assemblies 16a, 16b. Support arm assemblies 16a, 16b are used in place of ear loop sections which normally hook around the wearer's ear to secure eyeglasses 84 onto the wearer's head. In this embodiment, center sleeves 18a, 18b are attached to the distal ends 88a, 88b of temple arms 86a, 86b, respectively, and may be integrally formed with temple arms 86a, 86b from a single piece of resilient material such as polyethylene sheet, or may comprise separate portions which are joined together by adhesives, melt bonding, or like means. Support arm assemblies 16a, 16b are otherwise used in the same manner as related above for visor apparatus 10.

Figure 7:
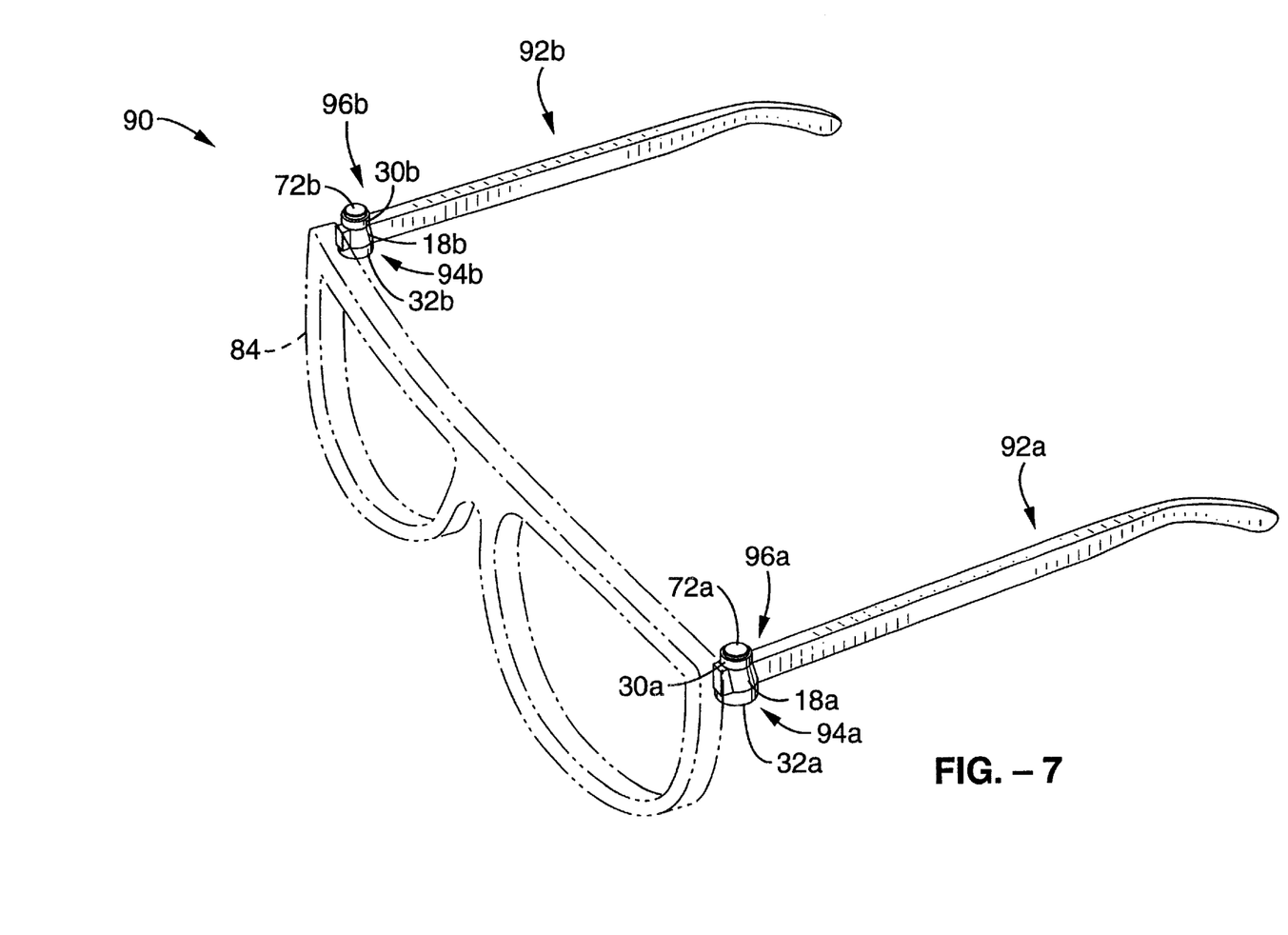
FIG. 7 is a perspective view of the articulating adjustment means of the present invention coupled to eyeglasses shown in phantom.

Referring also to FIG. 7, yet another alternate embodiment 90 of the present invention is generally shown, wherein like reference numerals denote like parts. Alternate embodiment 90 comprises a pair of support arm assemblies 92a, 92b pivotally attached to eyeglass frame 84. Pivotal adjustment means 94a, 94b comprises upper sleeves 30a, 30b and lower sleeves 32a, 32b disposed at the front end 96a, 96b of support arm assemblies 92a, 92b, center sleeves 18a, 18b attached to eyeglass frames 84, tabs 72a, 72b and plungers (not shown) inserted through upper sleeves 30a, 30b, lower sleeves 32a, 32b and center sleeves 18a, 18b. Pivoting and locking of support arm assemblies 92a, 92b function identically as previously discussed, however, to practically accommodate mounting directly onto eyeglass frame 84, pivotal adjustment means 94a, 94b is smaller than that disclosed for use with support arms assemblies 16a, 16b in FIG. 1 through FIG. 6 and fabricated from a metal or like material.

Accordingly, it will be seen that this invention provides support arms assemblies adaptable to visors or eyeglasses which allow not only a greater degree of positional adjustment and wearer comfort than has heretofore been available, but also the capability for maintaining the articulating members in a fixed position after such positional adjustments. Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. An articulating head worn support apparatus, comprising:
   a first and a second support arm assembly, at least one said assembly including an articulating member coupled to an articulating hinge assembly, said articulating hinge assembly comprising
   a first sleeve,
   a second sleeve,
   a plunger disposed within said first and second sleeves, and
   a lock and release mechanism configured for adjusting the position of said first sleeve in relation to said second sleeve in a ratcheting manner;
   said lock and release mechanism comprising
      a plurality of serrations longitudinally disposed on said plunger,
      a plurality of longitudinally disposed serrations within said first sleeve,
      said serrations within said first sleeve configured to engage said serrations on said plunger,
      an annular spring for biasing said serrations on said plunger against said serrations within said first sleeve, and
      a non-circular aperture formed within said second sleeve,
      wherein said plunger is configured such that insertion into said non-circular aperture renders said plunger rotatably immovable relative to said second sleeve.

2. An apparatus as recited in claim 1, further comprising means for retaining said plunger within said sleeves.

3. An apparatus as recited in claim 1, wherein said plunger has a tapered configuration.

* * * * *